United States Patent [19]
Misch et al.

[11] Patent Number: 5,823,777
[45] Date of Patent: *Oct. 20, 1998

[54] DENTAL IMPLANTS TO OPTIMIZE CELLULAR RESPONSE

[75] Inventors: Carl E. Misch, Dearborn, Mich.; Martha Warren Bidez; J. Todd Strong, both of Birmingham, Ala.

[73] Assignee: Biohorizons, Inc., Birmingham, Ala.

[*] Notice: The term of this patent shall not extend beyond the expiration date of Pat. No. 5,628,630.

[21] Appl. No.: 796,347

[22] Filed: Feb. 7, 1997

Related U.S. Application Data

[63] Continuation-in-part of Ser. No. 356,597, Dec. 15, 1994, Pat. No. 5,628,630.

[51] Int. Cl.⁶ ............................................. A61C 8/00
[52] U.S. Cl. ........................................................ 433/174
[58] Field of Search .................................... 433/174, 173, 433/175, 176, 172

[56] References Cited

U.S. PATENT DOCUMENTS

| | | | |
|---|---|---|---|
| 711,324 | 10/1902 | Lacy | 433/173 |
| 866,304 | 9/1907 | Roach | 433/173 |
| 2,112,007 | 3/1938 | Adams | 433/173 |
| 2,347,567 | 4/1944 | Kresse | 433/174 |
| 2,609,604 | 9/1952 | Sprague | 433/174 |
| 2,774,141 | 12/1956 | Quinn | 433/213 |
| 3,435,526 | 4/1969 | Brancato | 433/174 |
| 3,499,222 | 3/1970 | Linkow et al. | 433/174 |
| 3,729,825 | 5/1973 | Linkow et al. | 433/176 |
| 3,732,621 | 5/1973 | Bostrom | 433/174 |
| 3,787,975 | 1/1974 | Zuest | 433/182 |
| 3,849,887 | 11/1974 | Brainin | 433/173 |

(List continued on next page.)

FOREIGN PATENT DOCUMENTS

| | | |
|---|---|---|
| 0 073 177 | 8/1982 | European Pat. Off. . |
| 28 34 890 | 5/1979 | Germany . |
| 30 27 138 | 12/1981 | Germany . |
| 34 23 752 | 10/1985 | Germany . |
| 48-438 | 12/1973 | Japan . |
| 604 674 | 7/1975 | Switzerland . |
| 660342 | 11/1949 | United Kingdom . |
| 757487 | 1/1953 | United Kingdom . |
| 968672 | 1/1961 | United Kingdom . |
| 937944 | 7/1962 | United Kingdom . |
| 1 203 093 | 9/1967 | United Kingdom . |
| 1 291 470 | 11/1969 | United Kingdom . |
| 1 352 188 | 4/1971 | United Kingdom . |
| 1 544 784 | 4/1977 | United Kingdom . |
| 1 565 178 | 2/1978 | United Kingdom . |
| 2 063 680 | 11/1980 | United Kingdom . |
| 2 112 683 | 9/1982 | United Kingdom . |
| 2 117 641 | 2/1983 | United Kingdom . |
| 2 199 502 | 12/1987 | United Kingdom . |
| WO 85/04321 | 10/1985 | WIPO . |
| WO 86/01705 | 3/1986 | WIPO . |

*Primary Examiner*—John J. Wilson
*Attorney, Agent, or Firm*—Needle & Rosenberg, P.C.

[57] ABSTRACT

A dental implant for having a longitudinal axis for implanting in bone, has a crest module having a top end, a bottom end and a wall having an outer surface and a threaded section. The threaded section has a crestal end and an apical end, the crestal end abutting the bottom end of the crest module, a helical thread extending along a portion of the first section from a base end outwardly to a distal end. The threaded section also has a length, a major diameter being defined as the diameter of the threaded section measured at the distal end of the thread and a minor diameter being defined as the diameter of the threaded section measured at the base end of the helical thread. The major diameter is constant along the length of the threaded section, whereas a selected thread feature is chosen as a function of a selected biomedical characteristic. The selected thread feature could include the minor diameter, the thread pitch or the thread geometry. The selected biomedical characteristic is one of the location in the bone in which the implant is placed, the elastic modulus of the bone and the desired biomechanical response of the bone.

12 Claims, 7 Drawing Sheets

U.S. PATENT DOCUMENTS

| | | | |
|---|---|---|---|
| 3,849,888 | 11/1974 | Linkow | 433/176 |
| 3,919,774 | 11/1975 | Fishman | 433/224 |
| 4,016,651 | 4/1977 | Kawahara et al. | 433/174 |
| 4,053,982 | 10/1977 | Weissman | 433/225 |
| 4,109,383 | 8/1978 | Reed et al. | 433/72 |
| 4,177,562 | 12/1979 | Miller et al. | 433/174 |
| 4,180,910 | 1/1980 | Straumann et al. | 433/173 |
| 4,187,609 | 2/1980 | Edelman | 433/176 |
| 4,195,367 | 4/1980 | Kraus | 3/1.91 |
| 4,204,321 | 5/1980 | Scott | 433/177 |
| 4,259,072 | 3/1981 | Hirbayashi et al. | 433/173 |
| 4,290,755 | 9/1981 | Scott | 433/173 |
| 4,302,188 | 11/1981 | Driskell | 433/173 |
| 4,324,550 | 4/1982 | Reuther et al. | 433/174 |
| 4,334,865 | 6/1982 | Borle | 433/221 |
| 4,359,318 | 11/1982 | Gittleman | 433/173 |
| 4,416,629 | 11/1983 | Mozsary et al. | 433/174 |
| 4,431,416 | 2/1984 | Niznick | 433/174 |
| 4,468,200 | 8/1984 | Munch | 433/174 |
| 4,488,875 | 12/1984 | Niznick | 433/173 |
| 4,552,532 | 11/1985 | Mozsary | 433/173 |
| 4,573,922 | 3/1986 | Bello | 433/176 |
| 4,645,453 | 2/1987 | Niznick | 433/173 |
| 4,661,066 | 4/1987 | Linkow et al. | 433/176 |
| 4,668,191 | 5/1987 | Plischka | 433/174 |
| 4,713,004 | 12/1987 | Linkow et al. | 433/174 |
| 4,780,080 | 10/1988 | Haris | 433/173 |
| 4,842,518 | 6/1989 | Linkow et al. | 433/174 |
| 4,856,994 | 8/1989 | Lazzara et al. | 433/173 |
| 4,863,383 | 9/1989 | Grafelmann | 433/174 |
| 4,904,187 | 2/1990 | Zingheim | 433/173 |
| 4,908,030 | 3/1990 | Linkow et al. | 623/16 |
| 4,915,628 | 4/1990 | Linkow et al. | 433/173 |
| 4,932,868 | 6/1990 | Linkow et al. | 433/174 |
| 4,944,754 | 7/1990 | Linkow et al. | 623/16 |
| 4,960,381 | 10/1990 | Niznick | 433/174 |
| 4,995,810 | 2/1991 | Soderberg | 433/141 |
| 5,022,860 | 6/1991 | Lazzara et al. | 433/174 |
| 5,030,095 | 7/1991 | Niznick | 433/173 |
| 5,061,181 | 10/1991 | Niznick | 433/174 |
| 5,071,350 | 12/1991 | Niznick | 433/173 |
| 5,076,788 | 12/1991 | Niznick | 433/173 |
| 5,078,607 | 1/1992 | Niznick | 433/174 |
| 5,116,225 | 5/1992 | Riera | 433/173 |
| 5,178,539 | 1/1993 | Peltier et al. | 433/173 |
| 5,180,303 | 1/1993 | Hornburg et al. | 433/173 |
| 5,194,000 | 3/1993 | Dury | 433/173 |
| 5,195,891 | 3/1993 | Sulc | 433/173 |
| 5,195,892 | 3/1993 | Gersberg | 433/174 |
| 5,197,881 | 3/1993 | Chalifoux | 433/173 |
| 5,199,873 | 4/1993 | Schulte et al. | 433/174 |
| 5,205,745 | 4/1993 | Kamiya et al. | 433/173 |
| 5,205,746 | 4/1993 | Chanavaz | 433/174 |
| 5,209,659 | 5/1993 | Friedman et al. | 433/173 |
| 5,209,666 | 5/1993 | Balfour et al. | 433/173 |
| 5,221,204 | 6/1993 | Kruger et al. | 433/173 |
| 5,232,364 | 8/1993 | Rosen | 433/173 |
| 5,238,405 | 8/1993 | Marlin | 433/173 |
| 5,242,303 | 9/1993 | De Buck | 433/173 |
| 5,246,369 | 9/1993 | Poulmaire | 433/173 |
| 5,246,370 | 9/1993 | Coatoam | 433/173 |
| 5,254,005 | 10/1993 | Zuest | 433/173 |
| 5,259,759 | 11/1993 | Jorneus et al. | 433/173 |
| 5,269,685 | 12/1993 | Jorneus et al. | 433/174 |
| 5,269,686 | 12/1993 | James | 433/173 |
| 5,286,196 | 2/1994 | Brajnovic | 433/173 |
| 5,292,252 | 3/1994 | Nickerson et al. | 433/173 |
| 5,302,126 | 4/1994 | Wimmer et al. | 433/173 |
| 5,302,127 | 4/1994 | Crisio, Jr. | 433/173 |
| 5,302,128 | 4/1994 | Suga | 433/176 |
| 5,312,254 | 5/1994 | Rosenlicht | 433/173 |

DENTAL IMPLANTS TO OPTIMIZE CELLULAR RESPONSE

CROSS-REFERENCE TO RELATED APPLICATION

This is a continuation-in-part of our copending application Ser. No. 08/356,597 filed Dec. 15, 1994, now U.S. Pat. No. 5,628,630.

BACKGROUND OF THE INVENTION

1. Field of the Invention

The present invention relates to skeletal implants (such as dental implants) and more particularly to a method of designing skeletal implants that promote strain-induced bone tissue growth and maintenance over the entire bone contacting surface of the implant.

2. Description of the Prior Art

Skeletal implants have been used for the replacement of articular joints within the body (e.g. total hip arthroplasty), restoration of aesthetics (e.g. bony retention of ear prosthesis) and replacement of missing teeth (e.g. dental implants). One of the primary failure mechanisms for skeletal implants is implant loosening at the implant-to-tissue interface due to non-physiologic loading profiles.

Roughly 125 million individuals in the United States alone are missing some of their teeth. One approach to treating patients missing teeth is to supply them with removable dentures. Dentures have the disadvantage of not adequately loading their supporting bone (such as the mandible for lower dentures and the maxilla for upper dentures). An unloaded supporting bone experiences very little strain. When the supporting bone lacks a minimum level of strain, bone resorption occurs. This results in shrinkage of the supporting bone and can further result in related health and aesthetic problems.

Another approach to treating edentulous or partially edentulous patients is to place endosteal osteointegrated (the integration of bone tissue with the implant) implants in the supporting bone. Osteointegrated endosteal implants are alloplastic materials surgically inserted into a residual bony ridge to serve as prosthodontic foundations. Such implants serve as platforms for prosthetic devices. The introduction of osteointegrated dental implants has given edentulous and partially edentulous patients a more effective means to restore their ability to chew and to improve their appearance. Furthermore, osteointegrated implants functionally load the mandibular (or maxillary) bone into which they are implanted, thereby inducing strain in the bone under normal functional loading. Bone loss and resorption, which commonly occur with dentures, can thereby be minimized or avoided by maintaining a proper loading profile on the bone.

Two subcategories of endosteal implants include plate form implants and root form implants. A plate form implant is characterized by a flat, narrow plate typically placed in a horizontal dimension of the mandibular or maxillary bone. Root form implants are designed to be placed in a vertical column of bone. Root form implants include two types: cylinder-type root form implants, which are non-threaded cylinders pressed into holes drilled into the receiving bone, and screw-type root form implants, having a threaded outer surface which is screwed into a hole drilled into the receiving bone.

The cylinder root form implant may have design features which minimize rotation of the implant in the implanted bone (e.g. holes and grooves) as well as a textured surface, which promotes close bone apposition to the implant. A disadvantage of cylinder root form implants is that they take a long time to set properly, as the patient must wait until the surrounding bone has properly integrated with the implant before functionally loading the implant.

Screw root form implants are held to the surrounding bone by a threaded outer surface. The threaded surface provides initial stabilization of the implant to the surrounding bone and it facilitates macroscopic bone integration. Because they are screwed into the bone, screw root form implants may not require as much time as cylinder root form implants prior to functionally loading.

Current screw and cylinder root form implants have a disadvantage in that bone resorption commonly occurs in the crestal region of the implant due to excessive strain experienced by the bone in this region. Furthermore, other regions of the bone may not experience enough strain and resorption may also occur. Although a certain level of strain must be experienced by the bone to prevent bone resorption, too much strain can also result in bone resorption. If the supporting bone experiences less than 100 microstrain or more than 3000 microstrain, bone resorption will occur. On the other hand, a strain level between about 100 microstrain and 3000 microstrain can actually encourage bone growth.

Many common screw-type implants impart too much strain in some portions of the implant-bone interface (e.g. the crestal regions) and not enough strain in other parts of the interface. This results in non-uniform bone ingrowth and resorption, which further results in implant loosening. Roughly 10% to 15% of all dental implant patients must eventually return to the implantologist for revision surgery due to inadequate bone ingrowth, loosening, or structural failure of the implant. Revision surgery can be significantly more costly than primary surgery. Furthermore, it often leads to increased failure rates due to surgical complications involving decreased quality of available bone, or bacterial smear layers of contamination on the implant once bone loss occurs.

More than 24 cylindrical shaped and blade-shaped endosteal and transosteal implant systems are available on the market today. These devices include those made by NobelPharma USA, Inc. of Nobel Industries in Sweden developer of the Branemark system, an endosseous fixture which is one of the most popular in the U.S. and which has been given full acceptance by the American Dental Association (ADA). Other devices which have received provisional acceptance by the ADA include: Dentsply (previously Core-Vent) root forms, Oratronics blade implant, and Integral cylindrical implants by Calcitek.

Niznick (U.S. Pat. No. 4,431,416) discloses a combination root form implant having an intermediate section with peripheral threads to engage the bone. The lower end of the implant is hollow and has peripheral holes through which bone tissue may grow. The implant receives a denture which transmits bite force to the gum tissue, thereby reducing the transmission of such force to the implant. Because the Niznick device does not physiologically load the implanted bone, it does not provide strain-induced bone growth.

Friedman et al. (U.S. Pat. No. 5,209,659) discloses a dental implant having a cylindrical body portion and a threaded apical portion which does not exceed one-half of the length of the body. The threaded portion has sharp external cutting threads which do not extend beyond the diameter of the cylindrical portion.

Scortecci (U.S. Pat. No. 5,312,256) discloses a screw-type root form implant that employs a fine pitch thread with a plurality of interruptions of the thread, both of which serve to reduce the internal stress in the bone in order to avoid necrosis. Scortecci does not disclose an implant wherein strain is maintained within a predetermined range in order to encourage bone growth and to reduce resorption.

Weiss et al. (U.S. Pat. No. 4,997,383) discloses a blade-type dental implant with substantial planar areas on the front and rear surfaces of the implant which make bone contact produce optimal force absorption in areas of highest stress. Weiss et al., however, does not disclose an implant designed to produce a level of strain in the implanted bone that would promote bone growth.

Valen (U.S. Pat. No. 5,007,835) discloses a screw-type root-form implant having rounded screw threads to provide radial forces at points in contact with the bone. A separate tapping mechanism is also disclosed. Although Valen attempts to reduce bone necrosis by employing rounded threads, Valen does not disclose a means to ensure that strain in the bone surrounding the implant is maintained within a predetermined range.

None of these devices have been developed to stimulate and maintain bone strain levels over the entire surface area of the implant which promote osteointegration while minimizing bone resorption.

Several references disclose methods of maintaining and promoting bone growth by applying mechanical stimuli. Mcleod et al. (U.S. Pat. Nos. 5,103,806 and 5,191,880) describes a method for preventing osteopenia and promoting bone growth by applying a mechanical load to the bone tissue at relatively low magnitudes and at relatively high frequencies. Although these patents suggest that the disclosed methods can be used in conjunction with prosthetic implants, they do not propose a particular implant geometry or a method by which to derive such a geometry.

Lanyon, in Control of Bone Architecture by Functional Load Bearing, 7 *Journal of Bone and Mineral Research* S369–S375 (Supp. 2, 1992) describes the importance of local functional strains in the control of bone architecture. This article discusses the adaptation and maintenance of bone as being predominantly due to a conservational or "osteogenic" strain regime sustained at each location of concern within the skeletal system.

None of these references disclose a method of designing an implant which optimizes the geometry of the implant to provide the level of strain on the implanted bone required to maximize osteointegration and minimize bone resorption. Nor do any of these references disclose an implant design which provides the level of strain on the implanted bone required to maximize osteointegration and minimize bone resorption over the entire bone contacting surface area of the implant.

Thus, there exists a need for a method of designing an implant so that the implant creates in the implanted bone a level of strain which maximizes bone growth and which minimizes bone resorption over the entire bone contacting surface area of the implant.

There also exists a need for an implant that promotes maintenance of bone under functional loading conditions over the entire bone contacting surface area of the implant.

SUMMARY OF THE INVENTION

The present invention is an implant system, including a design method and an implant apparatus, that optimizes strain distribution to surrounding osseous tissues under functional loading conditions in order to promote strain-induced bone growth, promote maintenance of the bone, and reduce bone resorption over the entire surface area of the implant. In one preferred embodiment, the invention provides an implant system for a screw-type, root-form dental implant.

Essentially, the present invention implements a method for designing a prosthetic implant which enhances hard tissue response and bone growth in response to the functional demands placed on the implant. First the designer evaluates macro-design criteria based on a knowledge of the anatomical dimensional limitations, the mechanical properties of the tissue at the implant skeletal reception site, and the functional demands placed on the implant. The designer must then apply basic engineering principles, based on a knowledge of functional strain levels at the reception site that promote physiologic health to the macro-design in order to optimize the micro-design features that enhance strain induced bone growth. Finally, the designer refines the micro-design features in order to customize the skeletal implant for various regions of the reception site.

More specifically, the method involves the following steps: characterizing the patient's bone at the predetermined site with respect to the parameters of width, height, and elastic modulus; generating a macro-design, or large scale design, for the implant based on the measured width and height of the bone at the predetermined site and a desired biomechanical response for the implant. A micro-design is then determined for the implant based on the measured elastic modulus of the bone at the predetermined site whereby the implant produces a strain in the bone during functional loading of the implant that is within a predetermined range which promotes bone growth and minimizes bone resorption. The micro design involves modifying those parameters that affect the response of the surrounding bone tissue to the implant at the cellular level.

The physiologic forces exerted by the implant on the bone at the predetermined site during functional loading of the implant are identified and related to the strain experienced by the bone to create strain equations for normal strain and shear strain. The normal strain and shear strain equations are then applied using the characterization parameters of the bone as input to modify the general mechanical macro-design and thereby create a micro-design for the implant such that the normal and shear strain acting on the implanted bone minimizes resorption of the bone and enhances growth of new bone tissue adjacent the implant.

The geometry of the micro-design for the implant is optimized such that the strain in the bone is maintained within a predetermined range. This is done by relating the force imparted by the implant to the strain experienced by the bone to create strain equations for normal strain and shear strain and then applying the normal strain and shear strain equations using the characterization parameters as input.

If the implant is a dental implant, such as a screw-type root-form dental implant, the designer may first assign different types of bone commonly found in the mandible and maxilla to predefined groups, with each predefined group having defined average characteristics of width, height, density, and modulus of elasticity. Then, the designer designs the implant specific for each of the groups. The implant is optimized to produce the amount of strain that will promote bone growth and minimize resorption in a bone having the average characteristics for the predefined group for which the implant is designed. This enables a surgeon to characterize a patient's bone at an implant site, identify the predefined group that corresponds to the patient's bone, and select the implant design that corresponds to the predefined group into which the patient's bone characterization belongs.

Once the overall design is complete, optimization routines are used to refine the design in order to create micro-design features that are specific for each type of implant. Finite element analyses (FEA) may be performed on the micro-designs in order to validate the performance of each type of dental implant under functional loading. The FEA represents a feasible way to accommodate the considerable complexities (geometrical, material, and load-related) that characterize a real clinical situation. Once validation of the implants is complete, design drawings are produced for each type of implant so that fabrication plans may be drafted.

Such a device adapted for implanting into the existing bone of a patient and for attaching a dental prosthesis thereto has a crest portion having a bottom surface and an opposite top surface, the top surface being adapted for attaching the dental prosthesis thereto and a base portion having a crestal end, an apical end, and a core section with an outer surface, the crestal end being attached to the bottom surface of the crest portion. It also has a means on the base portion for securing the device within the existing bone which minimizes resorption of the existing bone and promotes growth of new bone tissue adjacent the device.

In one embodiment, the securing means has a continuous thread, beginning at a first end adjacent the apical end of the base portion and terminating in a second end adjacent the crestal end of the base portion, the thread forming a helix around the core section and extending radially outward from the outer surface of the core section terminating in a thread face having an outermost end of the thread face. The thread has a bone contacting surface area defined between the outer surface of the core section and the outermost end. The bone contacting surface area of the thread increases as the thread nears the crestal end, thereby increasing the surface area over which force is distributed from the implant to the surrounding bone. Also, the radial length of the thread from the outer surface of the core section to the outermost end of the thread face increases as the thread approaches the crestal end which also increases the bone contacting surface area of the thread as the thread approaches the crestal end.

The radius of the device defined by the centerline longitudinal axis of the base portion and the outermost end of the thread face is constant between the apical end of the base portion and the crestal end of the base portion. The core section may be conical, wider near the apical end and narrower near the crestal end.

The preferred embodiment may be adapted for implantation depending on the density of the bone being implanted. The number of turns of the thread per unit height is selected based on the density of the bone being implanted. In relatively dense bone, the implant should have relatively fewer turns of the thread per unit height than would implants adapted for implantation in relatively less dense bone. In relatively less dense bone, the implant should have relatively more turns of the thread per unit height than would implants adapted for implantation in relatively more dense bone.

Yet another aspect of the invention is a dental implant for having a longitudinal axis for implanting in bone, has a crest module having a top end, a bottom end and a wall having an outer surface and a threaded section. The threaded section has a crestal end and an apical end, the crestal end abutting the bottom end of the crest module, a helical thread extending along a portion of the first section from a base end outwardly to a distal end. The threaded section also has a length, a major diameter being defined as the diameter of the threaded section measured at the distal end of the thread and a minor diameter being defined as the diameter of the threaded section measured at the base end of the helical thread. The major diameter is constant along the length of the threaded section, whereas a selected thread feature is chosen as a function of a selected biomedical characteristic. The selected thread feature may vary along the length of the implant. The selected thread feature could include the minor diameter, the thread pitch or the thread geometry. The selected biomedical characteristic is one of the location in the bone in which the implant is placed, the elastic modulus of the bone and the desired biomechanical response of the bone.

It is an advantage of the invention in that the geometry of the thread creates the optimal strain level in the bone being implanted.

These and other advantages will become apparent from the following description of the preferred embodiment taken in conjunction with the following drawings, although variations and modifications may be effected without departing from the spirit and scope of the novel concepts of the disclosure.

DETAILED DESCRIPTION OF THE PREFERRED EMBODIMENTS

Figure 1:
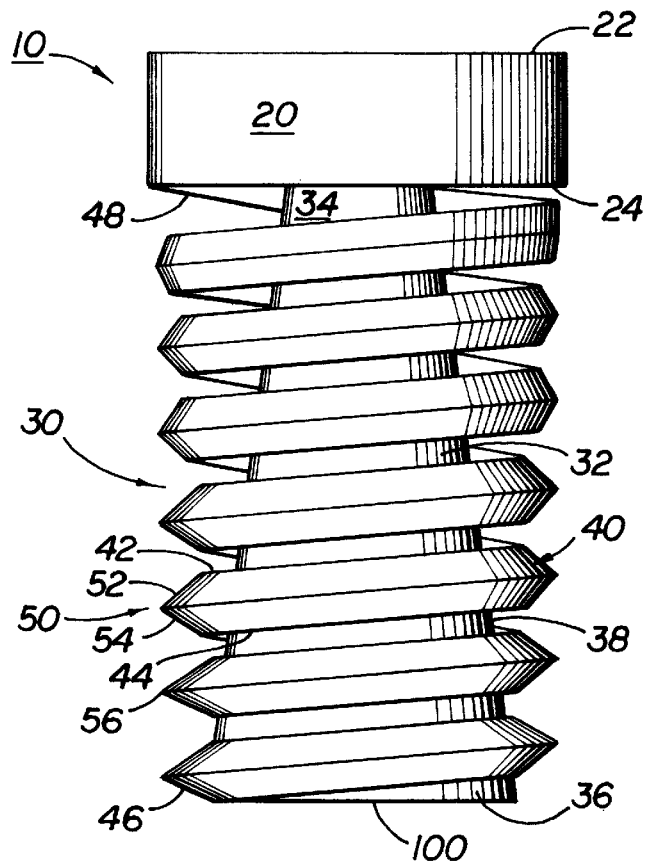
FIG. 1 is a side elevational view of an implant in accordance with the present invention designed for use as a dental implant.

A preferred embodiment of the invention is now described in detail. Referring to the drawings, like numbers indicate like parts throughout the views. As used in the description herein and throughout the claims that follow, "a," "an," and "the" includes plural reference unless the context clearly dictates otherwise. Also, as used in the description herein and throughout the claims that follow, the meaning of "in" includes "in" and "on" unless the context clearly dictates otherwise. Also, as used with respect to threads, "complimentary in shape" means generally having compatible thread dimensions, without necessarily having an identical thread shape.

One preferred embodiment of the present invention provides a method for designing a skeletal implant that is adapted for implantation in a patient's bone at a predetermined site. As used herein, the term "predetermined site" includes any of the possible sites in the body where a skeletal implant may be used (e.g., dental implants, etc.). First, the designer determines the patient's bone at the predetermined site with respect to the parameters of width, height, and elastic modulus; generating a macro-design, or large scale design, for the implant based on the measured width and height of the bone at the predetermined site and a desired biomechanical response for the implant. A micro-design is then determined for the implant based on the measured elastic modulus of the bone at the predetermined site whereby the implant produces a strain in the bone during functional loading of the implant that is within a predetermined range which promotes bone growth and minimizes bone resorption. The micro-design involves modifying those parameters that affect the response of the surrounding bone tissue to the implant at the cellular level.

The designer determines the micro-design for the implant based on the measured elastic modulus, using strain equations to ensure that strain in the bone is kept in a range to promote bone growth and to minimize bone resorption during functional loading. This is done by identifying the forces that will be imparted by the implant to the bone at the predetermined implant site and the strain that will be experienced by the bone resulting from the forces imparted by the implant. From this information, the implant designer creates strain equations. The strain equations are applied to the implant design using the characterization parameters of the bone as input to modify the general mechanical macro-design so that the amount of strain in the implanted bone will remain within the desired range.

With respect to dental implants, the different types of bone commonly found in the mandible and maxilla may be assigned to groups, each group having defined average characteristics of width, height, density, and modulus of elasticity. The implant designer is thus able to design an implant specific for each one of the groups, the implant being optimized to produce the amount of strain that will enhance new bone growth and osteointegration and minimize resorption in a bone having the average characteristics for the group for which the implant is being designed. The dental surgeon employing such an implant is thereby able to characterize a patient's bone, identify the assigned group and select the implant design that corresponds to the group into which the patient's bone characterization belongs.

Constraint values, based upon anatomical dimensional limitations (e.g buccal-lingual width and crestal height) and mechanical structure of the bone, are identified. These constraints are used to define constraint equations that relate the constraints to the physical forces imparted by the implant. After the constraint equations have been defined for specific regions of the mandible and maxilla, optimization routines are used to refine the macro-design in order to create micro-design features that are specific for each type of implant. The design may be validated by any method obvious to one skilled in the art of implant design. One such method is to perform finite element analyses (FEA) on the resulting designs, thereby validating the performance of each type of dental implant under physiologic functional loading. The FEA is performed on a computer using a program of the type known to those skilled in the art. Once validation of the implants is complete, design drawings are produced for each type of implant so that fabrication plans may be drafted.

Figure 3:
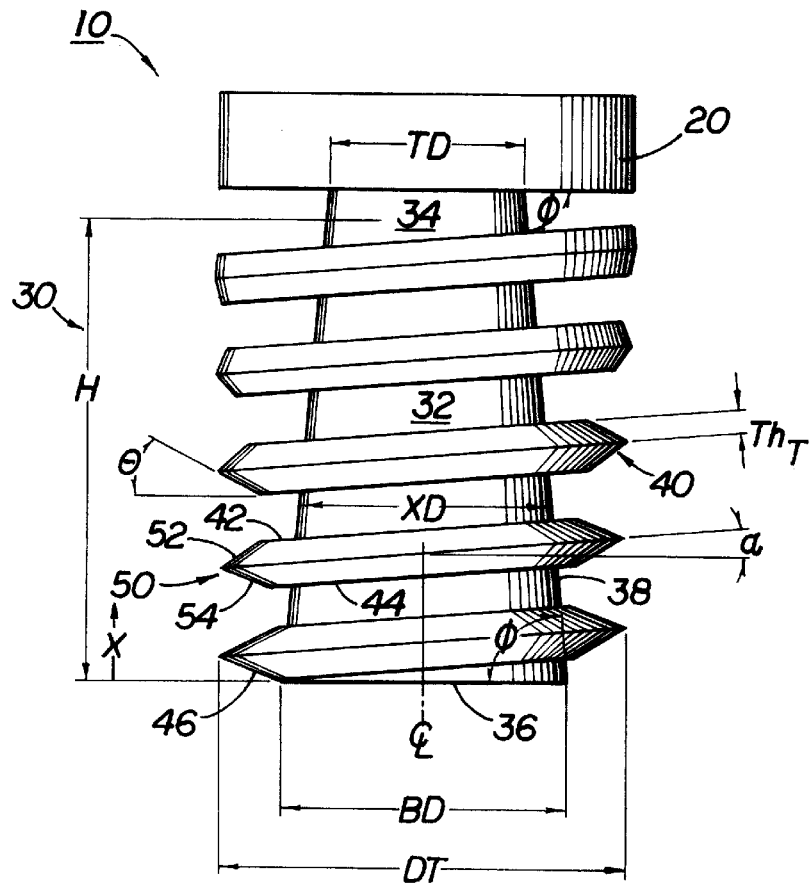
FIG. 3 is a side elevational schematic drawing of an implant in accordance with the present invention showing the angular and spacial relationships of the components therein.
Figure 4:
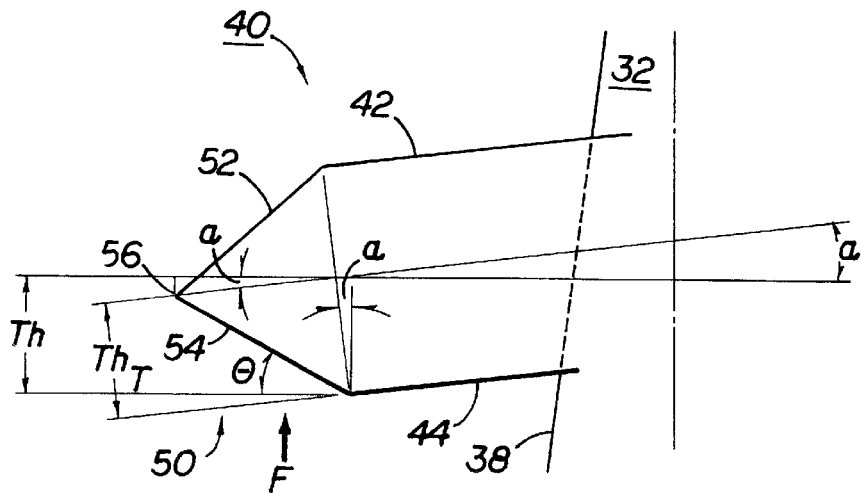
FIG. 4 is a cross-sectional schematic drawing of a portion of a thread showing its component angular and spacial relationships.

Referring to FIGS. 1, 3 & 4, a preferred embodiment of the apparatus of the present invention, designed for use as a dental implant 10, comprises a crest portion 20 attached to a base portion 30. The crest portion 20, provides a top surface 22 to which a prosthetic device (not shown) may be affixed. The crest portion 20 also has a bottom surface 24 which is attached to the base portion 30.

The base portion 30 provides a means to affix the implant to the patients mandible or maxilla. The base portion 30 comprises a substantially conical core section 32 and a thread 40 affixed to the core section 32. The core section 32 has a crestal end 34 affixed to the bottom surface 24 of the crest portion 20 and an opposite apical end 36.

The thread 40 is continuous and has a first end 46 and a second end 48 which forms a helix around the core section 32 from the apical end 36 to the crestal end 34. The thread 40 has a thread face 50 which is divided into an upper face 52 and a lower face 54 which are divided by the outermost end 56. The thread 40 extends radially outward from the outer surface 38 of the core section 32 and terminates at the outermost end 56 of the thread face 50. The thread face 50 also has an upper face ledge 42 and a lower face ledge 44.

Figure 2:
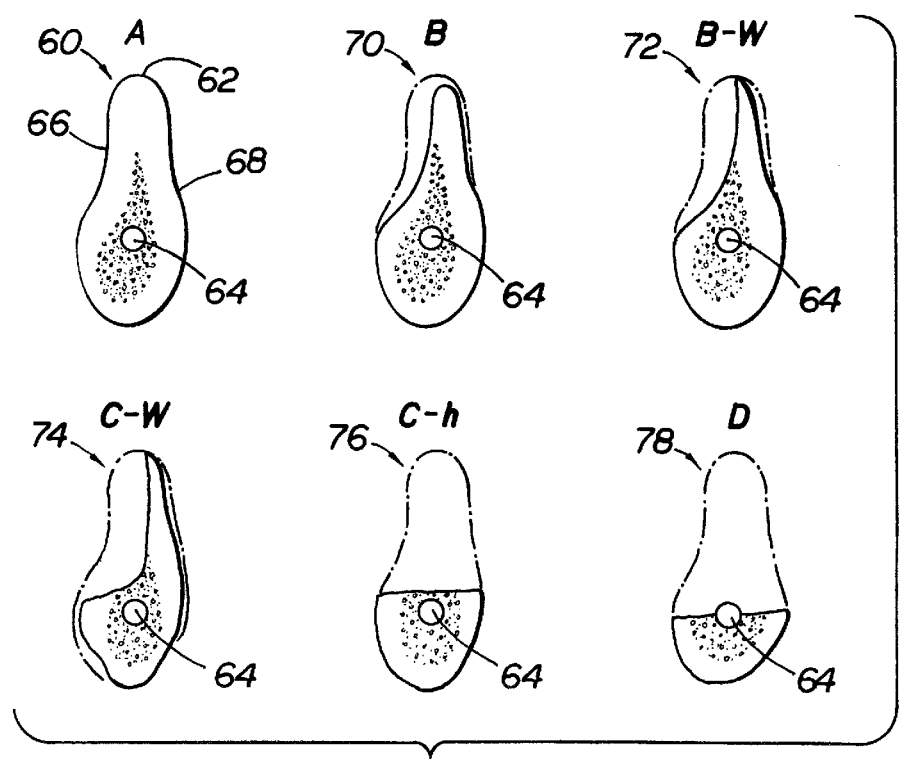
FIG. 2 is a chart showing a scheme of classifying the cross sectional area of available mandibular bone into several divisions.

The apical end 36 has a diameter that is smaller than the outside diameter of the thread 40 in order to allow the implant to have the self-tapping feature. The angle between the upper face edge 52 and the lower face edge 54 approaches 180 degrees as the thread 40 nears the crestal end 34, thereby increasing the surface area in the normal plane to the occlusal forces applied to the implant 10. This is necessary in light of the fact that the greatest amount of force applied to the implant 10 is orthogonal to the occlusal plane. Therefore, normal stresses are of greatest concern, especially in the crestal regions. The bottom surface 100 of the base portion 30 is flat in order to avoid opposing anatomical landmarks (e.g., the mandibular nerve canal as shown in FIG. 2, item 64) and to provide increased surface area in the normal plane to the applied force.

The implant 10 typically imparts most of the force that occurs as a result of functional loading in the crestal region of the bone. This induces the most strain in the crestal region, which frequently exceeds the physiologic strain levels resulting in bone resorption. Thus, it is desirable to distribute the force imparted on the crestal region of the bone by the implant 10 over a broader surface area, thereby inducing less strain in the crestal region of the implanted bone.

Therefore, in the implant 10 of the present invention, the total bone contacting surface increases as the thread 40 nears the crestal end 34. The bone contacting surface area of the thread comprises the surfaces of the upper thread ledge 42, the lower thread ledge 44, the upper face edge 52 and the lower face edge 54. The radial length of the thread 40 from the outer surface 38 of the core section 32 to the outermost end 56 of the thread face 50 increases as the thread 40 nears the crestal end 34. This is a result of both an increase in the angle between the upper thread face 52 and the lower thread face 54 as the thread nears the second end 48, and a narrowing of the core section 32 as it nears the crestal end 34. This increases the surface area over which force is distributed from the implant 10 to the surrounding bone, particularly in the crestal regions of the bone. By distributing the force over a greater surface area in the crestal regions, functional loading of the implant 10 results in less than about 3000 microstrain being induced by the implant 10 in the crestal region of the bone.

Conversely, the apical end 36 tends to induce less strain in the surrounding bone. If the implant 10 induces less than 100 microstrain the region of the bone near the apical end 36, new bone growth and osteointegration will occur at less than the optimal rate. Therefore, as the thread 40 nears the apical end 36, the radial length of the thread 40 from the outer surface 38 of the core section 32 to the outermost end 56 of the thread face 50 decreases. This is a result of a widening of the core section 32 near the apical end 36 and a decrease of the angle between the upper thread face edge 52 and the lower thread face edge 54. As the thread 40 nears the apical end 36, more strain is induced in the bone surrounding the apical end 36 of the implant 10. The implant 10 of the present invention thus induces strain of at least 100 microstrain in the surrounding bone, thereby promoting new bone growth and osteointegration.

The level of strain induced in the bone is a function of the stress imparted on the bone by the implant 10. In its simplest form, stress is equal to the magnitude of a force distributed over an area over which the force acts (Stress=Force/Area). Stress can be represented as either normal stress (perpendicular to the plane on which the force acts) or shear stress (parallel to the plane on which the force acts). Hooke's law relates normal stress and normal strain according to the following formula:

$$\sigma = E\epsilon$$

where:

$\sigma$=normal stress
E=modulus of elasticity
$\epsilon$=normal strain.

A similar relationship exists between shear stress and shear strain according to the following formula:

$$\tau = G\gamma$$

where:

$\tau$=shear stress
G=modulus of rigidity
$\gamma$=shear strain.

In order to maintain a uniform strain profile along the entire length of the implant 10, the stress profile must be uniform. Clinical experience has demonstrated crestal resorption surrounding root form dental implants. As has been shown in analytical studies, stresses are markedly increased in bone near the crestal regions of dental implants. This stress may be reduced in the crestal region by increasing the surface area in contact with the bone at the crestal region. In the preferred embodiment of the present invention, this area is progressively increased as the thread 40 approaches the top of the implant by using a gradually increasing thread depth. This concept is further enhanced by making the preselected angle, wherein the angle is a function of the vertical position of the thread along the length of the implant, between the upper face edge 52 and lower face edge 54 approach 180 degrees at a preselected rate, the rate being determined by the strain equations, as it advances to the top of the implant. However, in order to promote ease in the surgical process, the outside diameter of the implant must remain constant. By maintaining a constant outside diameter, the hole drilled into the bone for placement of the implant may have a constant inside diameter. Also, a constant outside diameter will allow the implant to have self-tapping threads which can engage the cortical plate for increased stability. This feature establishes the need for a tapered implant core. The tapered core enables the thread surface area to increase gradually toward the crestal region of the implant while the outside diameter remains constant.

In one preferred embodiment for a group of implants for posterior mandibles, the following classification of trabecular bone density are used to provide constraints for the design: D1, D2 (coarse), D3 & D4 (fine). The moduli of elasticity for the trabecular bone has been quantified for these densities.

As shown in FIG. 2, the various bone shapes of the mandible can be characterized into six divisions. Of these divisions, divisions A 60 and B 70 and are immediate candidates in the posterior mandible for using an implant in accordance with this preferred embodiment of the present invention. Divisions C-h 76, B-W 72, C-W 74, and D 78 would be candidates for this embodiment following bone grafting procedures. The available height, width and length of available bone must also be assessed for each patient. The height is measured from the crest 62 of the endentulous ridge to the opposing landmark (e.g. the maxillary sinus or mandibular canal 64). The width is measured from the facial plate 66 to the lingual plate 68 at the crest. The length is limited by adjacent teeth or other implants (not shown). The outside diameter of the implant depends on the width and length of the available bone.

Referring again to FIG. 1, the crest portion 20 is incorporated into the implant design in order to provide a point of attachment for a prosthesis (not shown) and to provide a crestal bone seal.

Although the above embodiment is tailored for screw root form dental implants, it should be appreciated by those skilled in the art that the disclosed method can be applied to other types of skeletal implants. These include hip implants, skull implants, and any type of skeletal implant in which maintaining a predetermined level of strain in the bone promotes osteointegration and reduces bone resorption under physiological functional loading.

Figure 5:
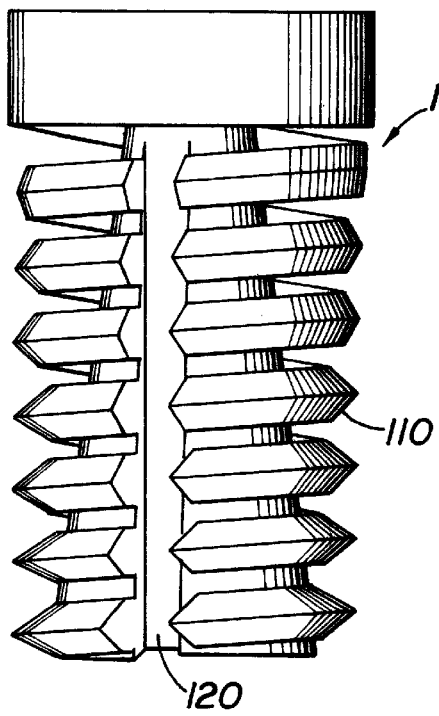
FIG. 5 is a side elevational view of a dental implant in accordance with the present invention having a groove transverse to the thread.

In an alternative preferred embodiment, as shown in FIG. 5, a dental implant 105 may comprise a groove 120, transverse to the thread 110, to prevent rotation of the implant 105.

Figure 6:
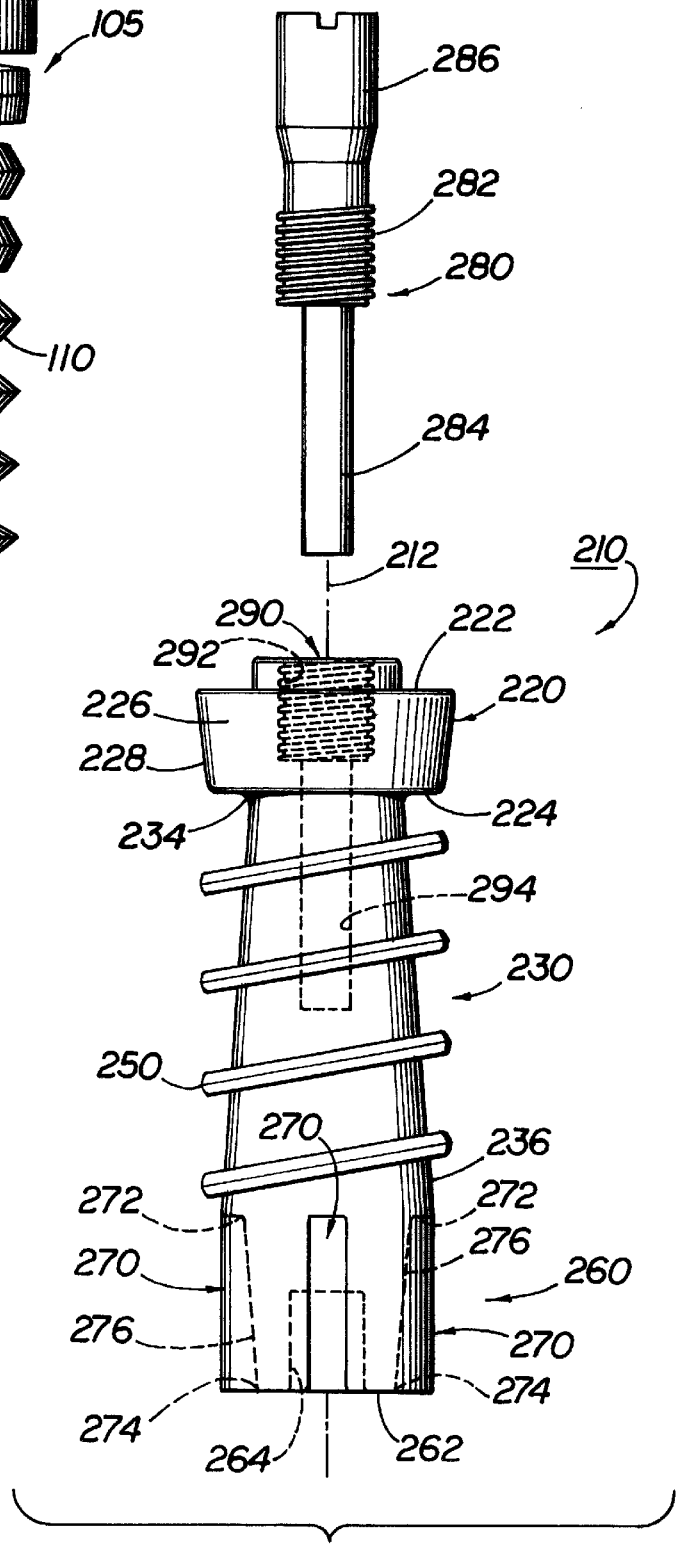
FIG. 6 is a side elevational view of an alternative preferred embodiment of a dental implant in accordance with the present invention.

As shown in FIG. 6, an alternative preferred embodiment of an implant 210 in accordance with the invention comprises a crest module 220 having a top end 222, a bottom end 224 and a wall 226 interconnecting the ends 222, 224 and having an outer surface 228. The outer surface 228 of the wall 226 is tapered toward the longitudinal axis 212 of the implant 210 from the top end 222 to the bottom end 224 so that a portion of any longitudinally directed force imparted on the implant 210 is distributed to the bone in a direction normal to the outer surface 228 of the wall 226.

A threaded first section 230 has a crestal end 234 and an apical end 236. The crestal end 234 abuts the bottom end 224 of the crest module 220. The threaded first section 230 defines a helical thread 250 extending from near the apical end 236 to near the crestal end 234.

Figure 7:
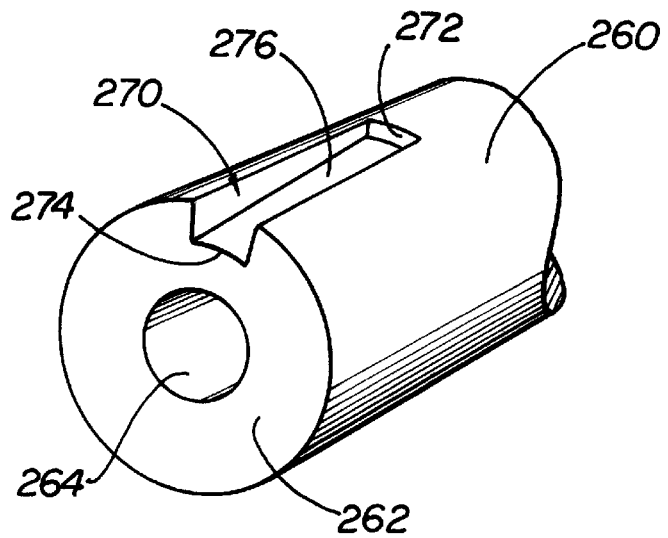
FIG. 7 is a perspective view of a the bottom section of an implant in accordance with the invention showing a recess and a round cavity therein.

A substantially cylindrical second section 260 extends longitudinally from the apical end 236 of the first section 230 and terminates in an end surface 262. The second section 260 defines at least one recess 270 along a portion of its length for receiving bone therein. (The embodiment shown in FIG. 6 employs four such recesses 270. However, as would be appreciated by one skilled in the art of implant design, many configurations of recesses 270 could be employed without departing from the scope of the invention. One such configuration could include many small, or even semi-microscopic recesses. Non-longitudinal recesses, such as spiral recesses, are possible.) As shown in FIG. 7, the recess 270 has a first end 272 and an opposite second end 274. An interior surface 276 extends from the first end 272 to the second end 274, with the interior surface 276 being tapered inwardly from the first end 272 to the second end 274 so that a longitudinally directed force imparted on the implant 210 is distributed to the bone in a direction normal to the interior surface 276. The end surface 262 of the second section 260 defines a centrally located cavity 264 that relieves fluid pressure in the implanted bone.

Figure 8:
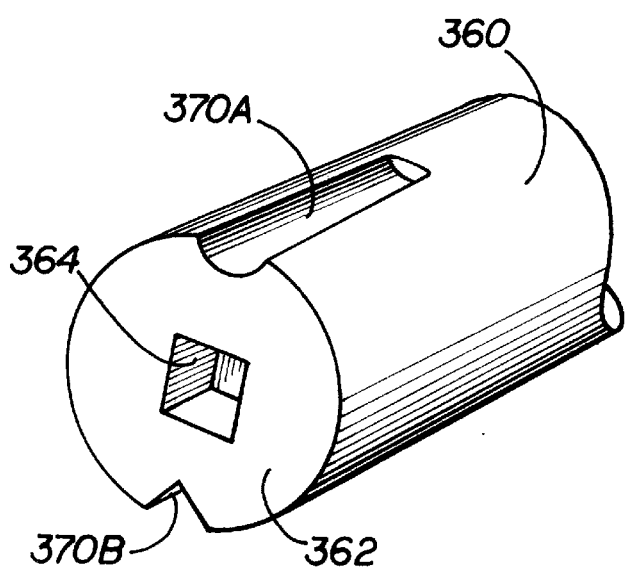
FIG. 8 is a perspective view of another embodiment of the bottom section of an implant in accordance with the invention showing a plurality of recesses and a non-round cavity therein.

As shown in FIG. 8, in alternative embodiments of the invention, several configurations of an inwardly tapered, longitudinally extending recess are possible on the second section 360. These include a curved recess 370a and a V-shaped recess 370b. Also, a non-circular cavity 364 can be employed to relieve fluid pressure from the bone near the end surface 362. A square cavity 364, for example, not only relieves fluid pressure, but also prevents implant rotation.

Returning to FIG. 6, the crest module 220 defines a longitudinally extending abutment screw bore 290. The surface of the bore has an interior threaded portion 292 defining a helical locking thread with an interior non-threaded portion 294 extending coaxially therefrom. An abutment screw 280 adapted for insertion into the abutment screw bore 290 has an exterior threaded portion 282, that is complimentary in shape to the interior threaded portion 292, and an exterior non-threaded portion 284 extending longitudinally therefrom. The interior non-threaded portion 294 is complimentary in shape to the exterior non-threaded portion 284 so that the interior non-threaded portion 294 is capable of receiving therein the exterior non-threaded portion 284 so as to aid in the alignment of the exterior threaded portion 284 of the abutment screw 280 with the interior threaded portion 292 of the abutment screw bore 290.

Figure 9:
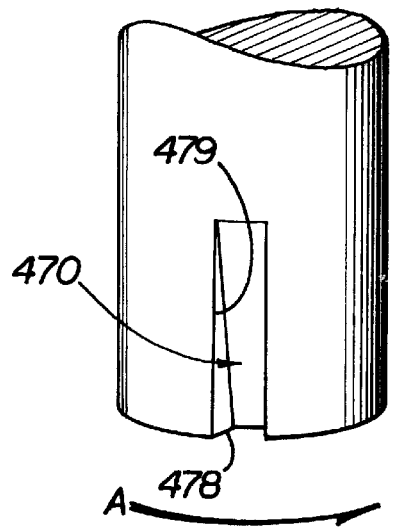
FIG. 9 is an side view of a further embodiment of the bottom section of an implant in accordance with the invention showing a recess having a cutting surface.

As shown in FIG. 9, the implant recess 470 may be provided with a means for removing bone from the inner surface of the hole as the implant is being implanted, so as to aid in conforming the shape of the hole to the shape of the implant. The bone removal means could comprise a first cutting surface 478 formed on the end of the recess 470 which extends through end surface 462 or a second cutting surface 479 formed on a longitudinal edge of the recess 470 adjacent the exterior surface of the second section 460, or both the first cutting surface 478 and the second cutting surface 479 may be employed. The cutting surfaces 478 and 479 are configured to remove bone as the implant rotates in the direction of arrow A.

Figure 10:
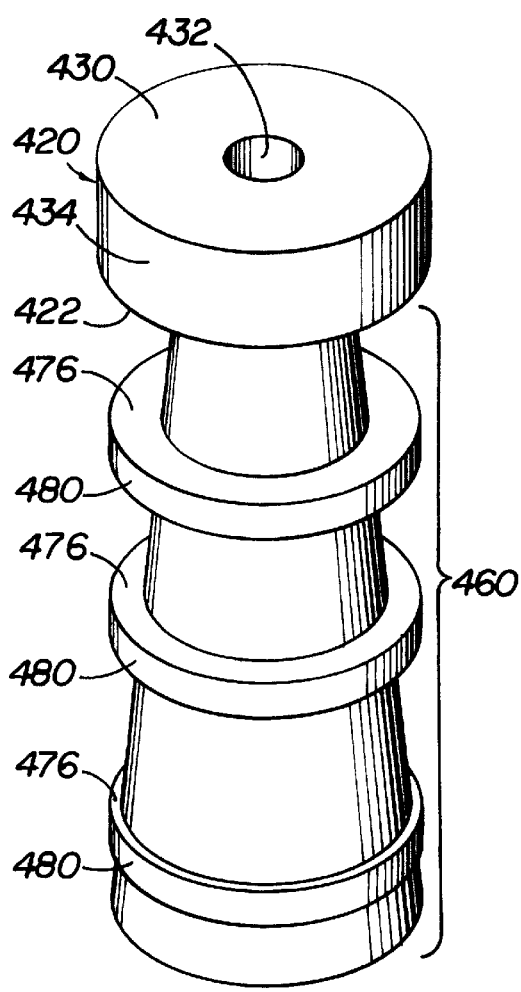
FIG. 10 is a perspective view of an implant employing rings for distributing force.

As shown in FIG. 10, in an alternative embodiment of the invention, the implant comprises a circular crest module 420 having a top surface 430 and an opposite bottom end 422, a sidewall 434 interconnecting the top surface 430 and the bottom end 422. The crest module 420 defines a bore 432 extending axially into the crest module 420 from the top surface 430. A section 460 extends longitudinally from the bottom end 422, tapering inwardly away from the bottom end 422, and a plurality of spaced apart rings 476 radially disposed along the length of section 460 so as to distribute a portion of any force imparted on the implant to the bone. Each ring has an outer surface 480 that, in one embodiment, is coextensive with side wall 434.

Figure 11:
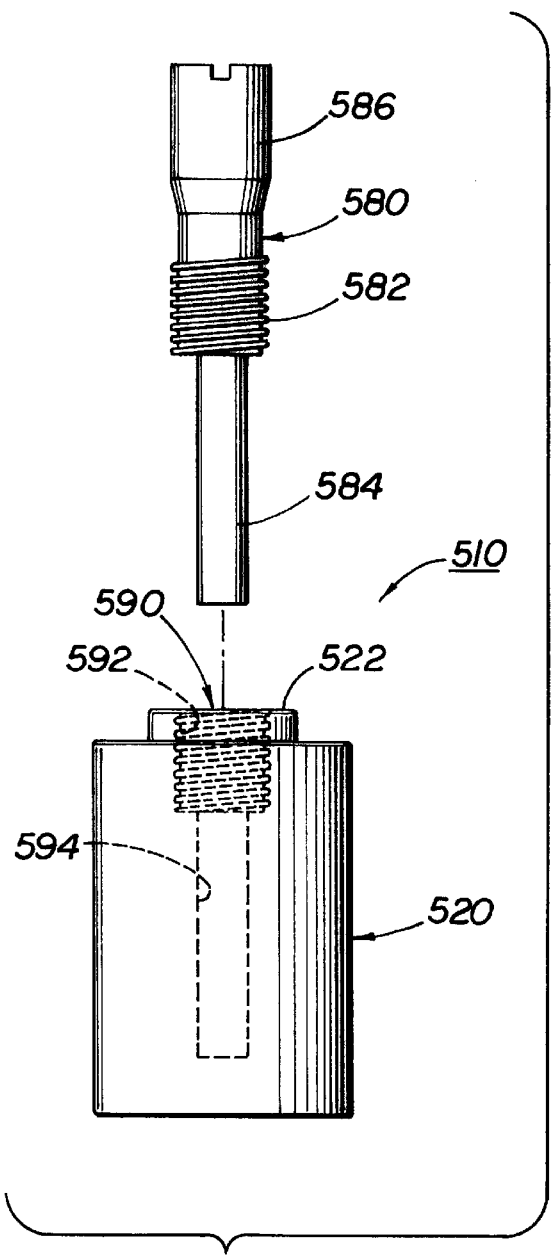
FIG. 11 is an exploded side view of a fastener in accordance with the invention.

As shown in FIG. 11, an alternative embodiment of the invention is a fastener 510 comprising an elongated male member 580 having an end portion 586, an external threaded portion 582 adjacent the end portion 586 and an external non-threaded portion 584 extending therefrom, the diameter of portion 582 being greater than the diameter of portion 584. A female member 520 has a first end 522 and defines an elongated bore 590 longitudinally extending from the first end 522. The bore 590 has an interior threaded portion 592 adjacent the first end 522 and an interior non-threaded portion 594 extending longitudinally from the interior threaded portion 592. The interior non-threaded portion 594 can receive therein the exterior non-threaded portion 584 so as to aid in the alignment of the exterior threaded portion 582 of the male member 580 with the interior threaded portion 592 of the female member 520.

It is possible to accelerate primary healing of bone contiguous to dental implants, accelerate consolidation of bone grafts, and assist in the integration of failing dental implants by applying additional stimulation to the implant. As a consequence of the treatment, the implant can be restored much sooner than would otherwise be possible, thereby, improving the quality of life for the edentulous patient. A device for applying stimulation to the implant, such as the Sonic Accelerated Fracture Healing System (SAFHS®) developed by Exogen, Inc. uses low-intensity, pulsed ultrasound to accelerate fresh fracture healing. The device may be prescribed by a physician and self-administered by the patient for daily 20 minute treatments.

Figure 12:
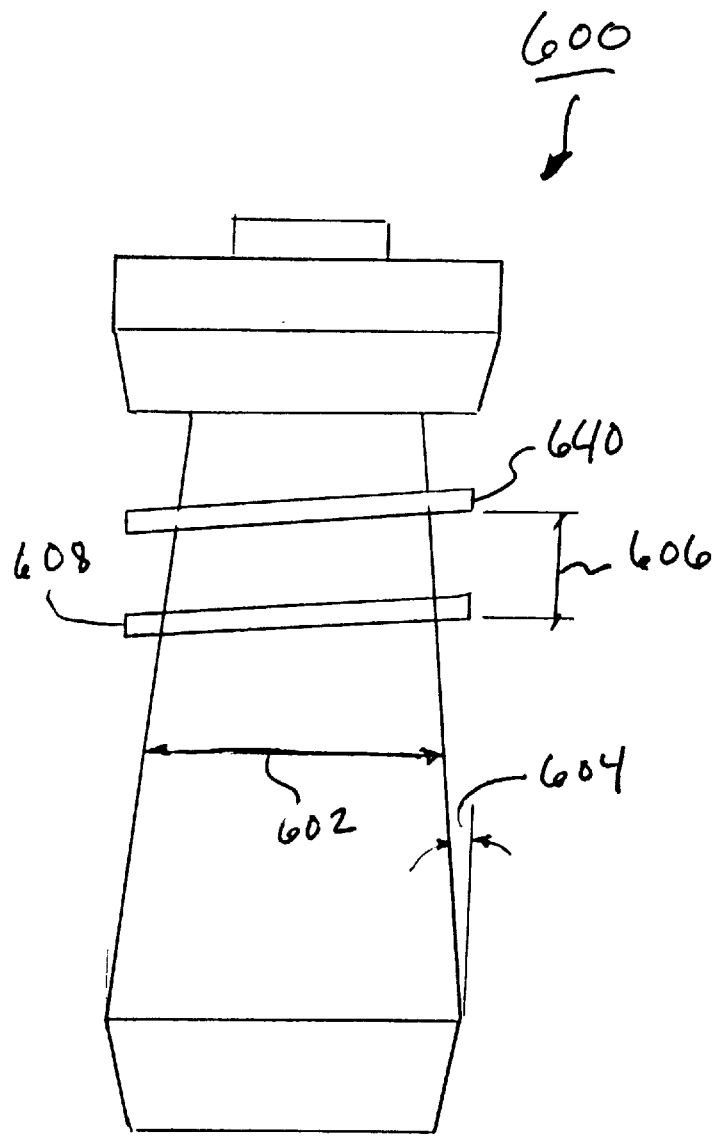
FIG. 12 is a schematic diagram of the invention showing the relationship of the thread features to the implant.

Referring to FIG. 12, various features of the thread 640 of the implant 600 may be varied as a function of a selected biomedical characteristic. These features include the minor diameter 602 (the minor diameter 602 manifesting itself as the angle 604 from vertical of the minor diameter), the thread pitch 606 (the pitch being the distance between iterations of the thread), and the geometric thread form 608 (the thread form being the outward geometric shape of the thread).

Figure 13:
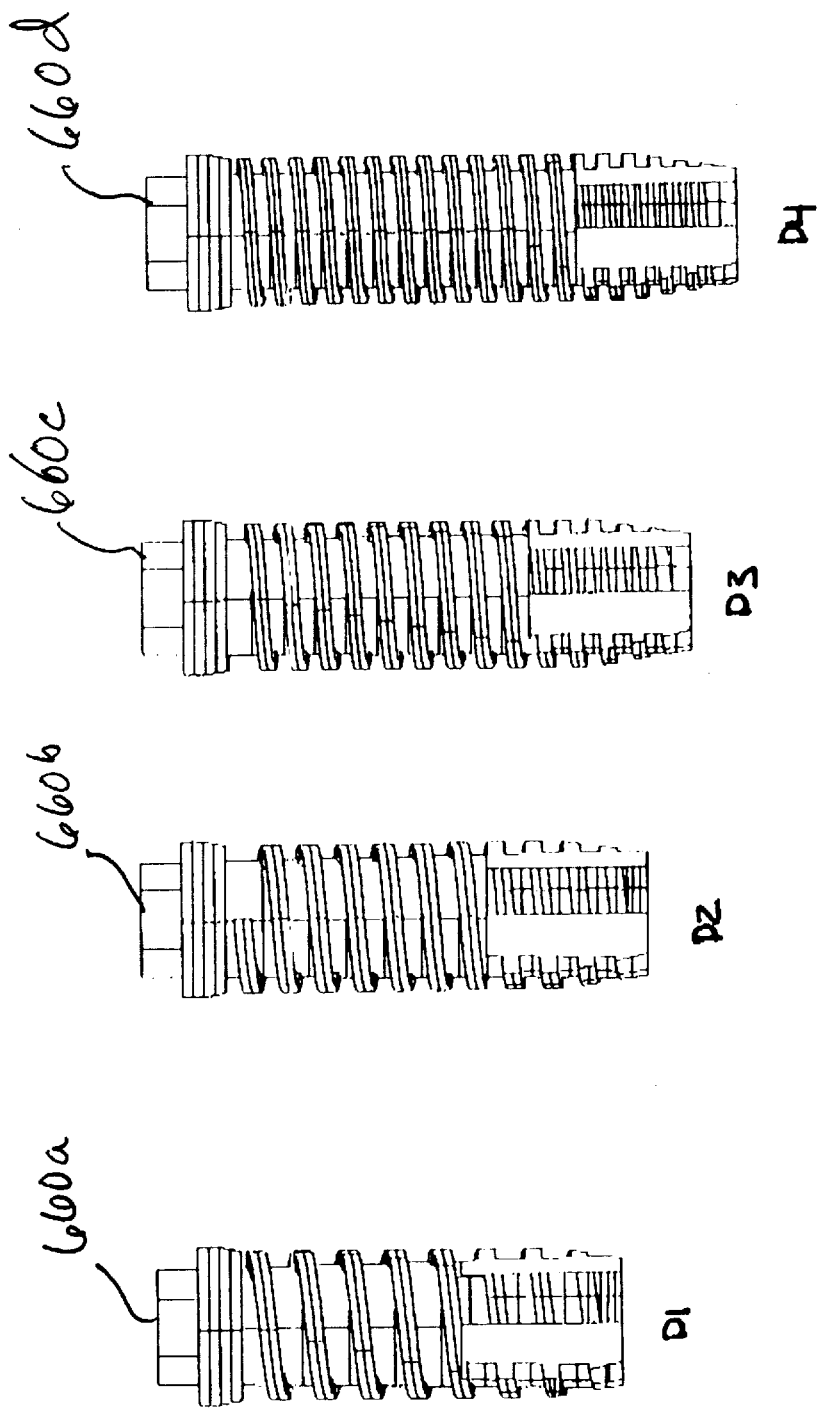
FIG. 13 is a schematic diagram of the invention showing a preferred embodiment of the invention configured for use with four different bone types.

As shown in FIG. 13, one commercial embodiment of the implant can take on different configurations, depending on the classification of the bone being implanted. For example, implant 660a is designed for implantation in D1-type bone, implant 660b is designed for implantation in D2-type bone, implant 660c is designed for implantation in D3-type bone and implant 660d is designed for implantation in D4-type bone.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. A dental implant having a longitudinal axis for implanting in bone, comprising:
   a. a crest module having a top end, a bottom end and a wall having an outer surface; and
   b. a threaded section having a crestal end and an apical end, the crestal end abutting the bottom end of the crest module, a helical thread extending along a portion of the threaded section from a base end outwardly to a distal end, the threaded section having a length, a major diameter being defined as the diameter of the threaded section measured at the distal end of the thread and a minor diameter being defined as the diameter of the threaded section measured at the base end of the helical thread, the major diameter being constant along the length of the threaded section, the minor diameter adjacent the crestal end being less than the minor diameter adjacent the apical end and the minor diameter varying along the length of the threaded section as a function of a selected biomedical characteristic.

2. The implant of claim 1, wherein the selected biomedical characteristic is the location in the bone in which the implant is placed.

3. The implant of claim 1, wherein the selected biomedical characteristic is the elastic modulus of the bone.

4. The implant of claim 1, wherein the selected biomedical characteristic is the desired biomechanical response of the bone.

5. The implant of claim 1, wherein the selected biomedical characteristic is the D1 through D4 bone classification of the bone.

6. A dental implant having a longitudinal axis for implanting in bone, comprising:
   a. a crest module having a top end, a bottom end and a wall having an outer surface; and
   b. a threaded section having a crestal end and an apical end, the crestal end abutting the bottom end of the crest module, a helical thread extending along the threaded section, the thread having a minor diameter, the minor diameter adjacent the crestal end being less than the minor diameter adjacent the apical end and the minor diameter, and the thread having a thread pitch that is selected as a function of a selected biomedical characteristic.

7. The implant of claim 6, wherein the selected biomedical characteristic is the location in the bone in which the implant is placed.

8. The implant of claim 7, wherein the selected biomedical characteristic is the D1 through D4 bone classification of the bone.

9. The implant of claim 6, wherein the selected biomedical characteristic is the elastic modulus of the bone.

10. The implant of claim 6, wherein the selected biomedical characteristic is the desired biomechanical response of the bone.

11. A dental implant having a longitudinal axis for implanting in bone, comprising:
   a. a crest module having a top end, a bottom end and a wall having an outer surface; and
   b. a threaded section having a crestal end and an apical end, the crestal end abutting the bottom end of the crest module, a helical thread extending along a portion of the threaded section from a base end outwardly to a distal end, the threaded section having a length, a major diameter being defined as the diameter of the threaded section measured at the distal end of the thread and a minor diameter being defined as the diameter of the threaded section measured at the base end of the helical thread, the major diameter being constant along the length of the threaded section, the minor diameter adjacent the crestal end being less than the minor diameter adjacent the apical end and the minor diameter varying along the length of the threaded section as a function of a first selected biomedical characteristic, the thread also having a thread pitch that is chosen as a function of a second selected biomedical characteristic, wherein the first selected biomedical characteristic and the second selected biomedical characteristic are selected from a group including: location in the bone in which the implant is placed, elastic modulus of the bone and desired biomechanical response of the bone.

12. The dental implant of claim 11, wherein the selected biomedical characteristic varies along the length of the thread.

\* \* \* \* \*